(12) United States Patent
Billman

(10) Patent No.: US 12,174,093 B1
(45) Date of Patent: *Dec. 24, 2024

(54) SYSTEMS AND METHODS FOR DETECTING, REPORTING, AND/OR USING INFORMATION ABOUT A BUILDING FOUNDATION

(71) Applicant: United Services Automobile Association (USAA), San Antonio, TX (US)

(72) Inventor: Bradly Jay Billman, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/545,566

(22) Filed: Dec. 19, 2023

Related U.S. Application Data

(63) Continuation of application No. 18/046,812, filed on Oct. 14, 2022, now Pat. No. 11,868,099, which is a continuation of application No. 16/411,367, filed on May 14, 2019, now Pat. No. 11,507,035, which is a continuation of application No. 12/471,097, filed on May 22, 2009, now Pat. No. 10,331,092.

(51) Int. Cl.
*G01M 5/00* (2006.01)
*E02D 33/00* (2006.01)
*G01N 25/72* (2006.01)
*G01N 33/38* (2006.01)

(52) U.S. Cl.
CPC ............ *G01M 5/0033* (2013.01); *E02D 33/00* (2013.01); *G01N 25/72* (2013.01); *G01N 33/383* (2013.01); *E02D 2600/10* (2013.01); *G01M 5/00* (2013.01)

(58) Field of Classification Search
CPC .. E02D 33/00; E02D 2600/10; G01N 33/383; G01N 25/72; G01M 5/0033; G01M 5/00
See application file for complete search history.

(56) References Cited

U.S. PATENT DOCUMENTS

| | | | | |
|---|---|---|---|---|
| 5,842,148 A | * | 11/1998 | Prendergast | G01M 5/0016 702/42 |
| 6,282,362 B1 | * | 8/2001 | Murphy | H04N 5/9201 358/909.1 |
| 7,180,404 B2 | * | 2/2007 | Kunerth | G01M 5/00 340/505 |
| 7,637,166 B2 | * | 12/2009 | Hecht | E02D 5/22 73/803 |
| 8,382,369 B2 | * | 2/2013 | Piscsalko | G01K 1/026 73/803 |

(Continued)

*Primary Examiner* — Freddie Kirkland, III
(74) *Attorney, Agent, or Firm* — BakerHostetler

(57) ABSTRACT

Cracks in foundations may be detected by sensing motion within the foundation. Depth sensors may be applied to a foundation, and the depths of the sensors may be read. At subsequent points in time the depths of the sensors may be read again. If the depths of the sensors are changing in a way that suggests that portions of the foundation are moving apart from each other, then it may be inferred that a crack is forming in the foundation. The formation of cracks may be used to take various actions. For example, the owner of the building that rests on the foundation may be information of the crack so that he or she may take remedial action.

20 Claims, 7 Drawing Sheets

(56) References Cited

U.S. PATENT DOCUMENTS

| | | | |
|---|---|---|---|
| 8,410,924 B2* | 4/2013 | Costanzo | G01M 5/0091 340/539.1 |
| 8,860,399 B2* | 10/2014 | Girlando | H04Q 9/00 307/104 |
| 8,919,057 B1* | 12/2014 | Dupray | E04B 5/36 52/223.6 |
| 8,990,027 B2* | 3/2015 | Hovhanessian | E02D 1/08 702/41 |
| 9,977,008 B2* | 5/2018 | England | G01K 13/10 |
| 10,042,341 B1* | 8/2018 | Jacob | H04L 12/2818 |
| 10,087,596 B2* | 10/2018 | Vuyk, Jr. | E02D 27/08 |
| 10,331,092 B1* | 6/2019 | Billman | G06F 18/00 |
| 10,892,558 B1* | 1/2021 | Wolynski | H01Q 9/16 |
| 11,507,035 B1* | 11/2022 | Billman | G06F 3/0487 |
| 11,868,099 B1* | 1/2024 | Billman | G01L 1/2262 |
| 12,025,608 B2* | 7/2024 | Takeuchi | G01M 5/0033 |
| 2003/0040934 A1* | 2/2003 | Skidmore | G06Q 40/08 707/999.107 |
| 2004/0128034 A1* | 7/2004 | Lenker | G05D 7/0635 700/282 |
| 2005/0207848 A1* | 9/2005 | Kunerth | G01M 11/30 405/129.1 |
| 2006/0283236 A1* | 12/2006 | Trescott, Jr. | G01M 3/002 374/4 |
| 2007/0028698 A1* | 2/2007 | Guziak | A61B 5/0215 73/729.2 |
| 2007/0074580 A1* | 4/2007 | Fallah-Rad | G01M 5/0008 73/786 |
| 2007/0095160 A1* | 5/2007 | Georgeson | G01N 29/0645 73/866 |
| 2007/0282541 A1* | 12/2007 | Griess | H04Q 9/00 702/33 |
| 2010/0175484 A1* | 7/2010 | Saigh | G01M 5/0083 73/775 |
| 2010/0201378 A1* | 8/2010 | Costanzo | G01M 5/0091 324/636 |
| 2012/0161789 A1* | 6/2012 | Girlando | G01N 33/38 29/592.1 |
| 2015/0276702 A1* | 10/2015 | England | G01K 13/10 374/4 |
| 2018/0100282 A1* | 4/2018 | Vuyk, Jr. | E02D 27/08 |
| 2018/0363267 A1* | 12/2018 | Vuyk, Jr. | E02D 27/08 |

* cited by examiner

SYSTEMS AND METHODS FOR DETECTING, REPORTING, AND/OR USING INFORMATION ABOUT A BUILDING FOUNDATION

CROSS-REFERENCE TO RELATED APPLICATION

This Application claims priority to and is a continuation of U.S. patent application Ser. No. 18/046,812, filed Oct. 14, 2022, which is a continuation of U.S. patent application Ser. No. 16/411,367, filed May 14, 2019, now U.S. Pat. No. 11,507,035, which issued on Nov. 22, 2022, which is a continuation of U.S. patent application Ser. No. 12/471,097, filed May 22, 2009, now U.S. Pat. No. 10,331,092, which issued on Jun. 25, 2019 and is incorporated herein by reference in its entirety.

BACKGROUND

The foundations of buildings, which are generally made of concrete or other forms of masonry, are subject to cracking. Foundations may be slab foundations, or the walls of basements, on top of which building structures rest. Cracking may be caused by factors such as seasonal changes in temperature and humidity, exposure to ground moisture, mechanical pressure from supporting a structure built on top of the foundation, seismic activity, or other types of stresses. Often, after some number of years, the foundation cracks as a result of these stresses.

One aspect of foundation cracks is that they typically start small and then accelerate. In many cases, building owners are unaware of a crack until the crack has become severe, at which point the crack may be costly to fix, or may be irremediable.

Foundation cracks may be detected by placing one or more sensor devices in or near the foundation, and using the sensors to monitor for spatial changes in the foundation. The position of the sensors could be recorded at the time the foundation is created, or at some other point in time at which the foundation is known to be in good condition. The positions of the sensors could then be read at later points in time to determine if the sensors are moving. If the sensors indicate that different portions of the foundation are moving apart from each other, a determination may be made that a crack is developing. The sensors could have sufficient sensitivity such that a crack might be detected before it is visible.

In one example, positional sensors could be spread throughout a concrete foundation before the concrete cures, thereby providing a three-dimensional view of the concrete. In another example, sensors could be applied to a surface of a foundation (e.g., along the wall of a basement, along the top of a slab, etc.), and the positions of the sensors in the two spatial dimensions along the surface could be recorded. Additionally, such sensors could be configured with depth-sensing capability, so that the two-dimensional arrangement of the sensors could provide three-dimensional information about the position of various points in the foundation.

Information about the condition of a foundation could be used as a service to a building owner (e.g., to provide early warning of foundation problems). Or, as another example, the information could be used to assist in insurance underwriting (or issuance of warranties), in order to assess certain risks to an insured or warranted building.

This summary section is provided to introduce a selection of concepts in a simplified form that are further described below in the detailed description section. This summary section is not intended to identify key features or essential features of the claimed subject matter, nor is it intended to be used to limit the scope of the claimed subject matter.

DETAILED DESCRIPTION

Figure 1:
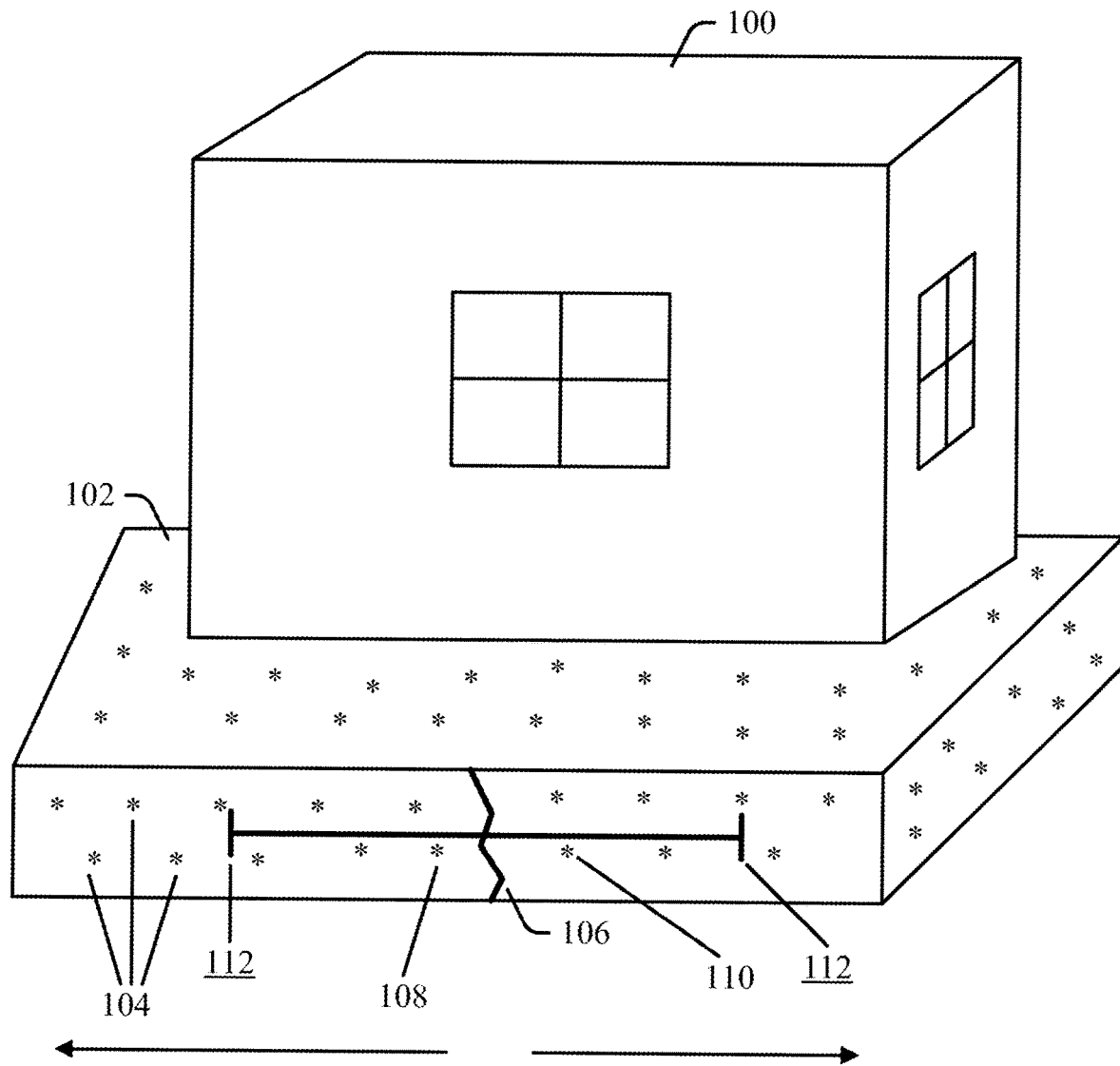
FIG. 1 is a perspective view of an example of a building that rests on an example foundation.

Building foundations are typically made of concrete or other masonry material. Foundations are often subject to cracking, due to seasonal changes in temperature and humidity, exposure to ground moisture, mechanical pressure from supporting a structure built on top of the foundation, seismic activity, or other types of events. The typical progression of a crack is that it starts small, and then accelerates. At the outset of a crack, it may not be visible to the naked eye.

The effect of having a crack in a building foundation can range from a minor nuisance to a catastrophe. For example, a crack may allow water to seep into a basement, or may attract mold and mildew. Or, in a more severe example, a cracked foundation may be unable to continue to support the building on top of it, causing a collapse.

Early detection of cracks may aid in repair and/or in keeping down the cost of repair. Some cracks may pass a "point of no return," after which they are not repairable. Even if a large crack is repairable, the repair might have cost less if the crack had been detected early.

The subject matter described herein provides a way to detect foundation cracks. Sensors may be applied to a foundation. Mechanisms may be used to detect motion of the sensors, even motion that occurs in very small amounts over large periods of time. If the motion of the sensors suggests that different sections of the foundation are separating from each other (or have already separated from each other), it may be inferred that the foundation has cracked or is in the process or cracking. The information gathered from the sensors may be used for various purposes—e.g., to warn the building owner so that the owner can take appropriate remedial action, to make decisions about underwriting insurance or issuing a warranty, or for any other reason.

There are various ways to apply sensors to a foundation. In one example, sensors that are capable of determining and communicating their position relative to other sensors could be mixed into concrete (or other building foundation material, or other foundation material) before the concrete (or other building foundation material, or other foundation material) is poured into a foundation. In another example, an electrical grid could be formed through the foundation, thereby allowing changes in position to be detected through disturbances in the electrical or magnetic field formed by the grid.

In yet another example, sensors could be applied to a surface of the foundation, and their positions could be recorded. The positions of the sensors along the surface would allow motion of the foundation to be detected in two dimensions. Additionally, the sensors along the surface could be configured with depth-sensing capabilities, thereby allowing these sensors to detect motion of the foundation in the direction that is parallel to the surface.

There are various ways that sensors could be applied along a surface of a foundation. In one example, some foundations are lined with a foam surface, and sensors could be embedded in the foam. However, even in the absence of a foam surface, a layer could be applied to the surface of the foundation in order to allow sensors to be installed along the foundation's surface.

Information about a cracking foundation could be used in various ways. For example, the building's owner could be warned about a cracking foundation before the crack is visually detectable, thereby allowing the owner to solve the problem at a lower cost and before the problem becomes irremediable. Or, as another example, a company that is interested in issuing a warranty on the building could use the readings from the sensors to assess the risk associated with the foundation. Such a company might even insist that such sensors be installed so that it can detect problems early, thereby (possibly) lowering the repair cost for problems for which the company would be responsible. In some cases, information about the foundation could be used for insurance underwriting. While many insurance policies do not cover structural damage, there may be risks associated with a building that has a cracked or cracking foundation, and an insurance company could take this information into account when deciding whether to insure a building, or when deciding what premium to charge. For example, a building with a cracked foundation may be more subject to damage in an earthquake. Or, a building that is about to collapse due to an irremediably cracked foundation may be at especially high risk for owner-initiated arson.

Turning now to the drawings, FIG. 1 shows an example of a building that rests on a foundation. Building 100 could be any type of building—e.g., a house, an office building, a skyscraper, a nuclear power plant, a restaurant, etc. Foundation 102 is underneath building 100, and it provides support for building 102. Building 100 remains in place on foundation 102 due to gravity and friction, although there is typically some type of fastener (e.g., bolts) that resist lateral movement of building 100 across foundation 102. In the example of FIG. 1, foundation 102 is shown as a slab foundation, although foundation 102 could take any form. As one additional non-limiting example, foundation 102 could be the walls and/or floor of a basement, which would serve as a foundation in the sense that building 100 could rest on the tops of the walls.

Foundation 102 may be made of any type of material. Typically, foundations are made of concrete, although foundations may be made of other types of material, such as stone, bricks, etc. Although foundations are normally made of a masonry material, foundations could also be made of other types of materials. For example, building technology could progress to the point that foundations could be made of a synthetic polymer or other material. The subject matter herein may be used with any type of foundation made of any kind of material.

Sensors 104 may be applied to foundation 102. In the example of FIG. 1, sensors 104 (each of which is shown by an asterisk), are applied to foundation 102 by interspersing them throughout the material of which foundation 102 is made. This configuration of sensors 104 is an example; as depicted in subsequent drawings, it is also possible to apply sensors to a surface of a foundation rather than interspersing them throughout the foundation's material.

Sensors 104 may be implemented through various mechanisms. In one example, sensors 104 are Radio Frequency Identification (RFID) tags, which respond to electromagnetic energy within a certain frequency by reflecting a code. A reader receives the codes. Each tag may have a different code, so that the presence of a tag may be determined based on the reflected code. By applying energy to the foundation at different angles, the positions of the RFID sensors could be determined by triangulation, thereby allowing the three-dimensional positions of the sensors to be determined.

Other implementations of sensors 104 could also be used. For example, sensors 104 could be electrically-powered transmitters that are powered by long-life batteries, and that transmit energy at some portion of the electro-magnetic spectrum. Or, the sensors could be electrically-powered by wires that run through the foundation, thereby reducing the risk of battery failure. As with the RFID tags, each sensor could have a distinguishing number associated therewith, so that each different sensor could be identified. Moreover, as with the RFID tags, the positions of the sensors could be determined by reading the energy coming from the sensors at different angles, thereby allowing the positions of the sensors in three-dimensional space to be determined by triangulation.

The foregoing are some example implementations of the sensors, although any implementation could be used. The subject matter herein is not limited to any particular implementation of the sensors.

Over time, crack 106 may form through foundation 102. Crack 106 may be formed by pressure, temperature changes, groundwater, or by any other cause. Regardless of the reasons for which crack 106 forms, crack 106 may represents a hazard to the structural integrity of foundation 102. For purposes of illustration, the example of FIG. 1 shows crack 106 as being visible, although crack 106 could form before it becomes visible to the naked eye.

Since crack 106 runs more-or-less vertically through foundation 102, crack 106's existence could be detected by changes in the positions of sensors 104. For example, as crack 106 forms, sensors 108 and 110 may grow further apart from each other, since they are on opposite sides of crack 106. The technology that is used to read sensors 104, 108, and 110 may have some amount of measurement error—i.e., given readings of the sensors taken at two different points in time, it is possible that differences in the readings are due to accuracy limits on the technology that is used to determine the position of the sensors. However, if the relative position of these sensors exceeds the measurement error, then it could be inferred that sensors 108 and 110 have moved relative to each other, which tends to indicate the existence of, or nascent formation of, crack 106. The arrows in FIG. 1 show how sensors on opposite sides of crack 106 might experience motion in opposite directions, and this motion could be detected by evaluating the positions of the sensors.

Figure 2:
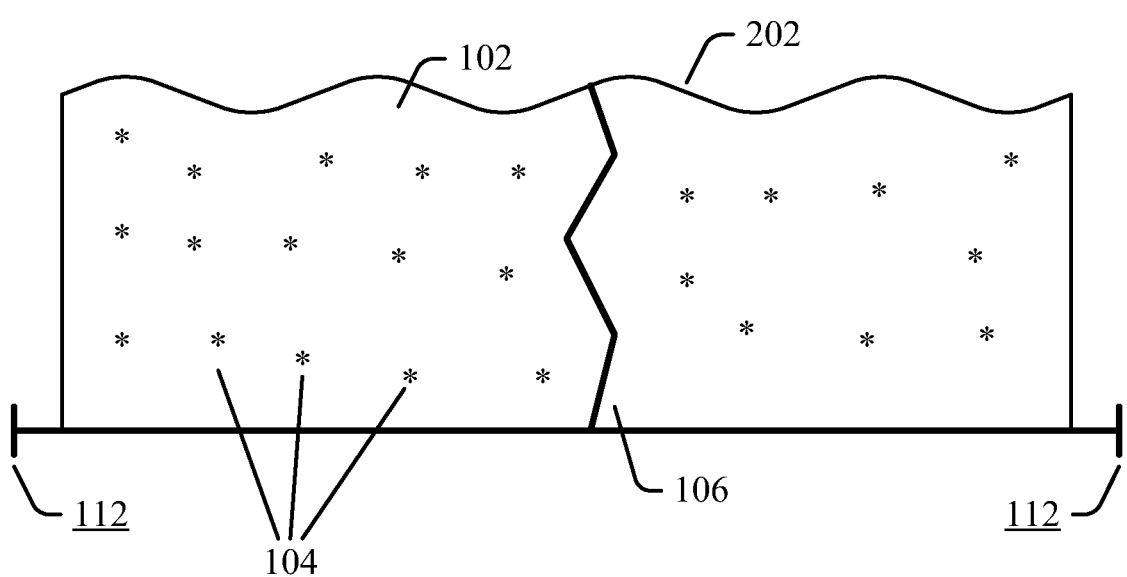
FIG. 2 is a sectional view of the foundation shown in FIG. 1, taken along line 112-112.

FIG. 2 is a sectional view of foundation 102, taken along line 112-112 (as shown in FIG. 1).

As can be seen in FIG. 2, sensors 104 are located throughout foundation 102. Line 112-112 is located along the perimeter of foundation 102 (as shown in FIG. 1). Wavy line 202 represents a region of foundation 102 that lies near the center of the foundation. Thus, as can be seen in the example of FIG. 2, sensors 104 may be located not only near the surface of foundation 102, but also at interior points. Sensors 104 are shown as being interspersed in a regular pattern through foundation 102, although sensors 104 could be located in an irregular pattern.

Crack 106 is visible in FIG. 2. In FIG. 1, crack 106 is visible only on the surface of foundation 102, but, as can be seen in FIG. 2, crack 106 proceeds through to the interior of foundation 102. Thus, any of sensors 104 that are on opposite sides of crack 106 may move apart from each other so as to facilitate detection of crack 106.

Figure 3:
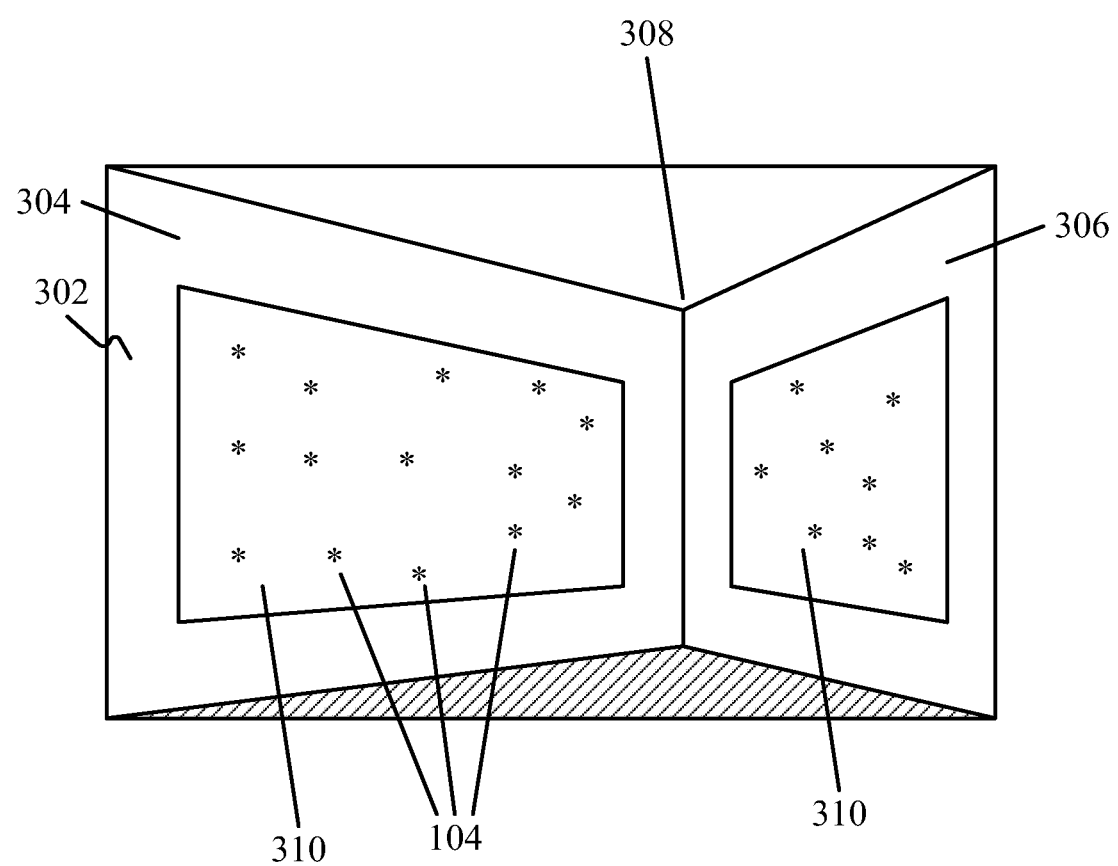
FIG. 3 is a perspective view of an example foundation, in which sensors are embedded in a surface material.

FIG. 3 is a perspective view of an example foundation in which sensors are embedded in a surface material. In the example of FIG. 3, foundation 302 is the walls of a basement. A building may rest on these walls, so the walls function as a foundation. The perspective shown in FIG. 3 may be understood as a view looking toward the far corner of a basement. Thus, foundation 302 has a first wall 304 and a second wall 306, joined by corner 308.

Each of the walls 304 and 306 that are part of foundation 302 is covered, in this example, by foam material 310. For example, foam material 310 may be a moisture-resistant foam that protects foundation 302 from damage due to water. Or, foam material 310 may be a thermally-insulating material that helps to stabilize the room temperature of the basement within walls 304 and 306. While a form material is shown, any type of material could cover walls 304 and 306, and the material could be used for any purpose. Moreover, while the example of FIG. 3 shows foam material 310 covering the surface walls of a basement-type foundation, foam material 310 (or any other type of material) could cover the surface of any foundation. As one non-limiting example, the slab foundation 102 (shown in FIG. 1) could have a surface covered by a foam material (or any other type of material).

The presence of a material on a surface of a foundation provides one way in which sensors could be mounted. In FIG. 3, sensors 104 are shown as being mounted in foam material. Mounting the sensors in a material that covers a surface of a foundation allows sensors to be used with a foundation without having to intersperse the sensors in the material. Thus, for example, if there is a reason to add sensors 104 to foundation 302 after the concrete of foundation 302 has already been poured, sensors may be added to foundation 302 by including them in a surface material, which may be accessible long after foundation 302 has cured.

Since sensors 104 are positioned along one or more planar surfaces of foundation 302, they may be used to detect cracks that cause lateral movement along that surface. While a crack that does not cause movement in any of these planes likely would not be detected through movement of the sensors, detection in these planes might be sufficient for many applications. Or, as an alternative, it may be possible for sensors positioned along a plane to be equipped with depth-sensing capability that allows motion to be detected outside of the planes in which the sensors are mounted. (FIG. 4, discussed subsequently, shows an example in which depth-sensing techniques are used to detect motion outside of the plane in which sensors are mounted.).

With sensors 104 mounted in foam material 310 along planar surfaces of foundation 302, cracks can be detected in much the same manner as discussed previously in connection with FIG. 1. If, over time, sensors 104 are changing position in a way that suggests that portions of foundation 302 are moving apart from each other, then it may be determined that a crack exists, or is developing, in foundation 302.

Figure 4:
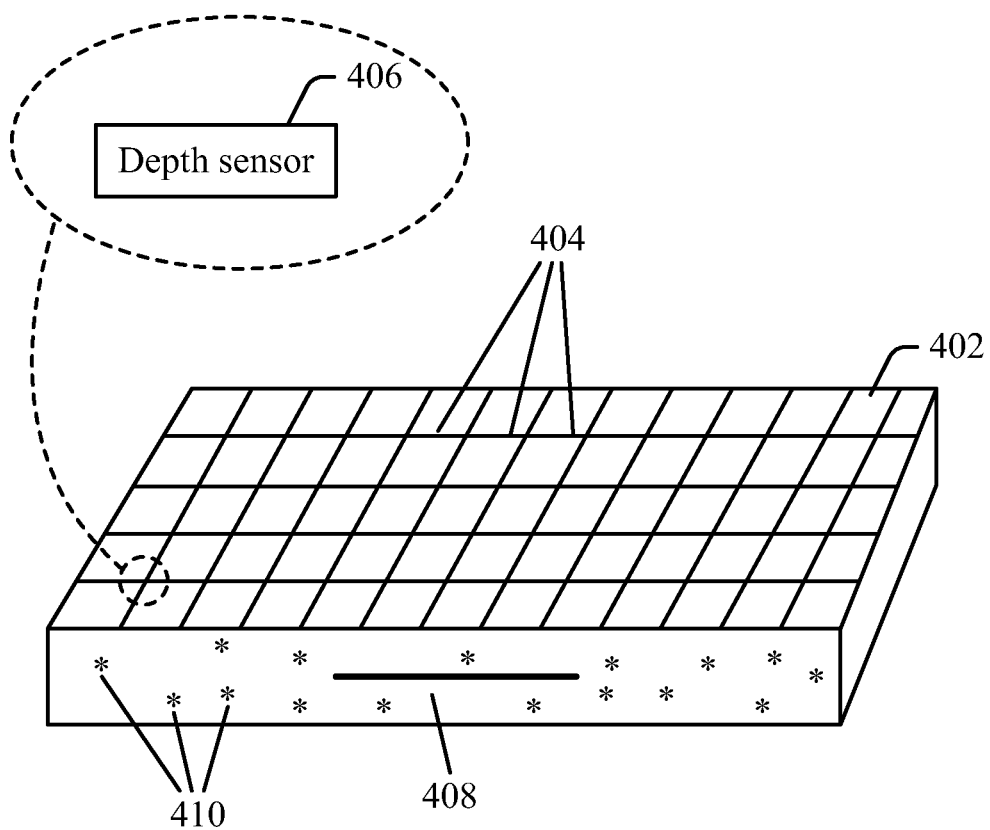
FIGS. 4 and 5 are perspective views showing foundations with example configurations of sensor.

FIG. 4 shows a foundation 402, with an example configuration of sensors. A material 404 is placed along a surface of foundation 402. In the example of FIG. 4, material 404 is placed along the top surface of foundation 402, although material 404 could be placed along any surface. Material 404 may take the form of a pad that is affixed to a surface, or could take some other form (e.g., a spray, a foam, etc.).

Material 404 is configured with devices that allow motion to be detected along the surface on which material 404 is placed. For example, sensors that record and/or transmit their position (e.g., sensors 104, shown in FIGS. 1-3) could be placed throughout material 404. Such a configuration would allow any separation of material 404 to be detected, and thus any motion of foundation 402 along the surface on which material 404 is mounted could be detected.

In order to detect motion that occurs not along the surface on which material 404 is mounted, material 404 could be configured with depth sensors, such as depth sensor 406. Depth sensors could be placed at regular or irregular locations along material 404. Depth sensors 406 could detect changes in the thickness of foundation 402, thereby allowing motion in foundation 402 to be detected even if that motion occurs in a direction perpendicular to the surface on which material 404 is mounted. For example, if a crack occurs along line 408, that crack will tend to push the top and bottom of foundation 402 apart in a vertical direction, which is perpendicular to the surface on which material 404 is mounted. Thus, such a crack may not cause any motion along that surface. However, depth sensors could detect that the thickness of foundation 402 is changing, thereby allowing the crack to be detected. In one example, device 410 may be located throughout foundation 402, and depth sensor 406 could interact with these devices. For example, depth sensor 406 might produce a burst of energy which could be reflected off devices 410, thereby allowing the locations of those devices (and any relative motion of the devices) to be sensed.

Figure 5:
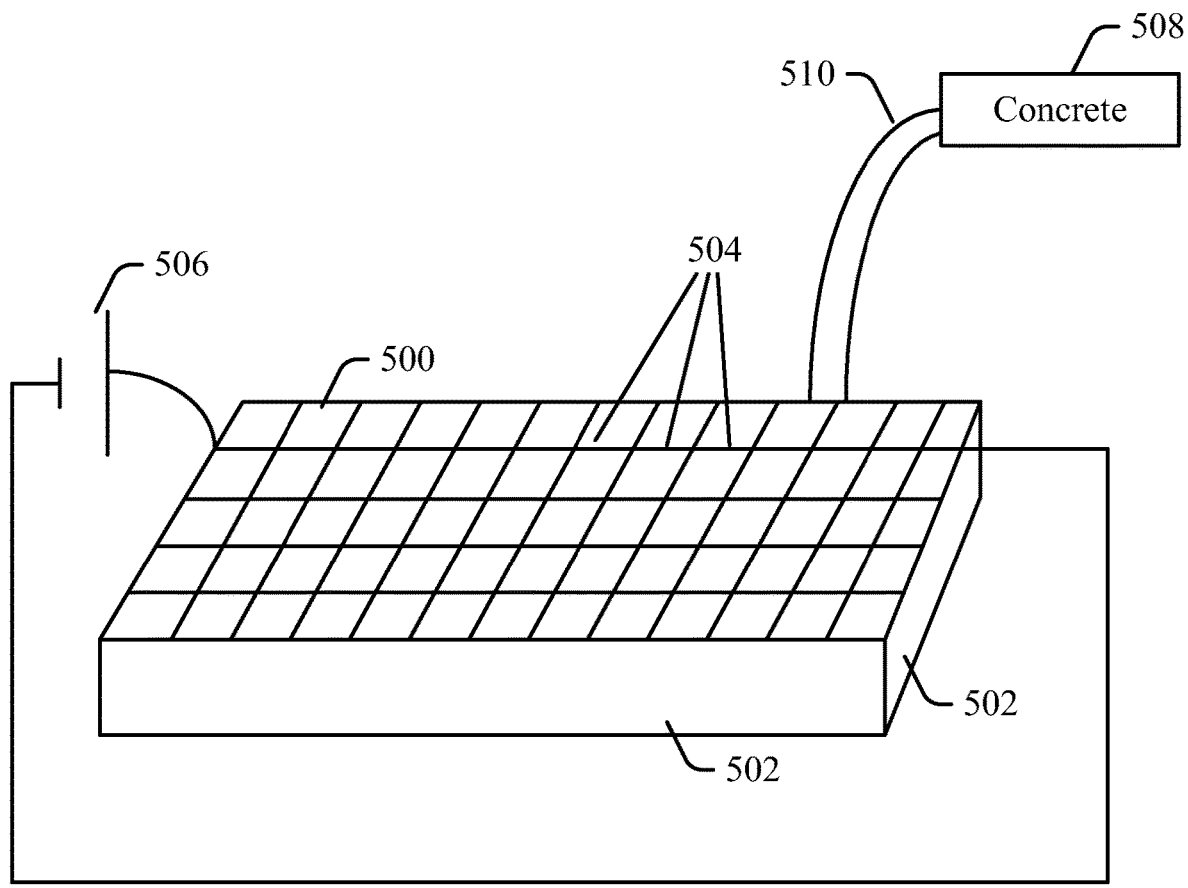

FIG. 5 shows yet another example of how sensors may be built into a foundation. Foundation 500 is a concrete foundation, which will be poured into forms 502. Before foundation 500 is poured, electrical wires 504 are placed throughout foundation 500 in a grid pattern. After foundation 500 is poured, a potential 506 may be applied to electrical wires 504, thereby creating a current through wires 504. In order to form foundation 500, concrete 508 is poured into forms 502 (as indicated by chute 510), thereby embedding wires 504 in concrete when the concrete cures.

When potential 506 is applied to the wires, current runs through the wires and electrical and magnetic fields are generated. If foundation 500 cracks, the wires will move relative to each other. By sensing deformities in the electrical field generated by wires 504, motion within foundation 500 may be detected, thereby allowing the presence of cracks in foundation 500 to be inferred.

Figure 6:
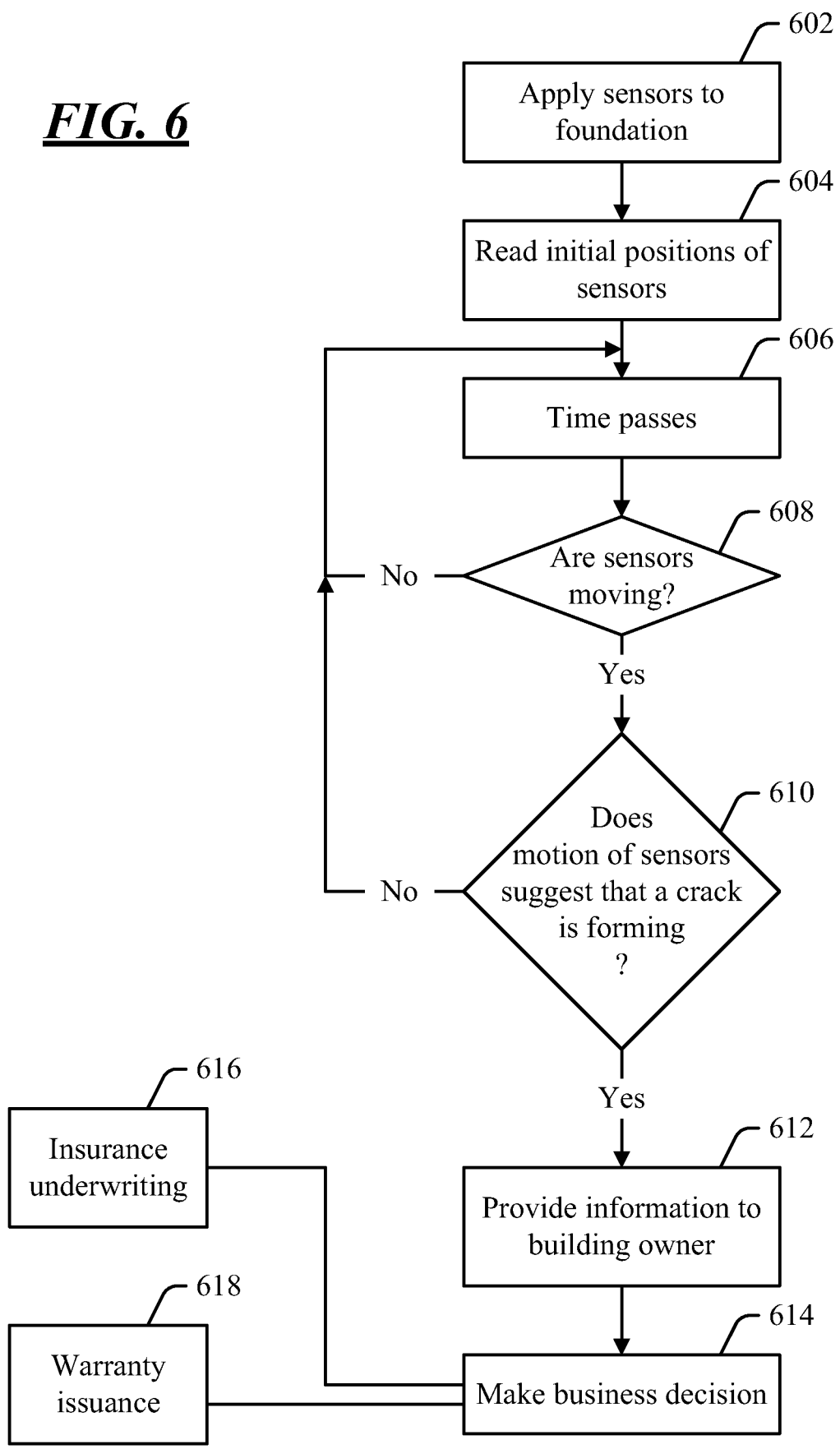
FIG. 6 is a flow diagram of an example process of detecting cracks in a foundation and/or taking action on the basis of such detection.

FIG. 6 shows, in the form of a flow chart, an example process of detecting cracks in a foundation and/or taking action on the basis of such detection.

At 602, sensors are applied to a foundation. The sensors may be applied, for example, using the techniques shown in FIGS. 1-5, which are described previously. At 604, the initial positions of the sensors are read and recorded. For example, the coordinates of each sensor's position in a plane, or in 3D space, may be recorded, and the coordinates may be stored for later comparison.

At 606, time passes. Cracks in foundations tend to develop over a period of months or years. Thus, it may take the passage of a significant amount of time before sufficient motion in the sensors could be detected to infer the existence of a crack.

At 608, it is determined whether the sensors are moving (or have moved) relative to their previously-recorded positions. If the sensors have not moved, then the process returns to 606, whereupon additional time passes.

If the sensors have moved, then it is determined, at 610, whether the motion that has been detected suggests that a crack is forming. Some amount of motion may be normal, or may be so minimal that it does not suggest the formation of a crack. Moreover, some readings of the sensors that appear to suggest motion may be due to measurement errors in determining the sensors' positions. Thus, not all detected changes in the sensors' positions implies that a crack is occurring. However, a change that is sufficient large, and that is corroborated by the motion of several different sensors, may suggest that a crack is occurring. (A crack in a foundation generally causes large portions of the foundation to separate. Thus, the motion of one lone sensor may suggest an error in the sensor rather than separation of the foundation due to a crack. However, if several sensors are moving in approximately the same direction, this fact may suggest that the foundation is separating and that a crack is occurring.).

If the detected motion does not suggest that a crack is occurring, then the process returns to 606 so that additional time may pass. On the other hand, if the motion suggests that a crack is occurring, then various actions may be taken. One example of such an action is to provide information to the owner of the building that rests on the foundation (at 612). For example, if the building is a house, the homeowner may want to know that his or her foundation is cracking. A company, such as the homeowner's insurance company, might provide this information as a service to its insureds.

Another example of an action that may be taken is to make a business decision based on the detected crack in the foundation. For example, an insurance company may make underwriting decisions on the basis of the cracking foundation (at 616). Or, as another example, a company that issues building warranties may determine whether to issue a warranty based on the severity of the crack, its reparability, the owner's willingness to fix the crack, etc.

Figure 7:
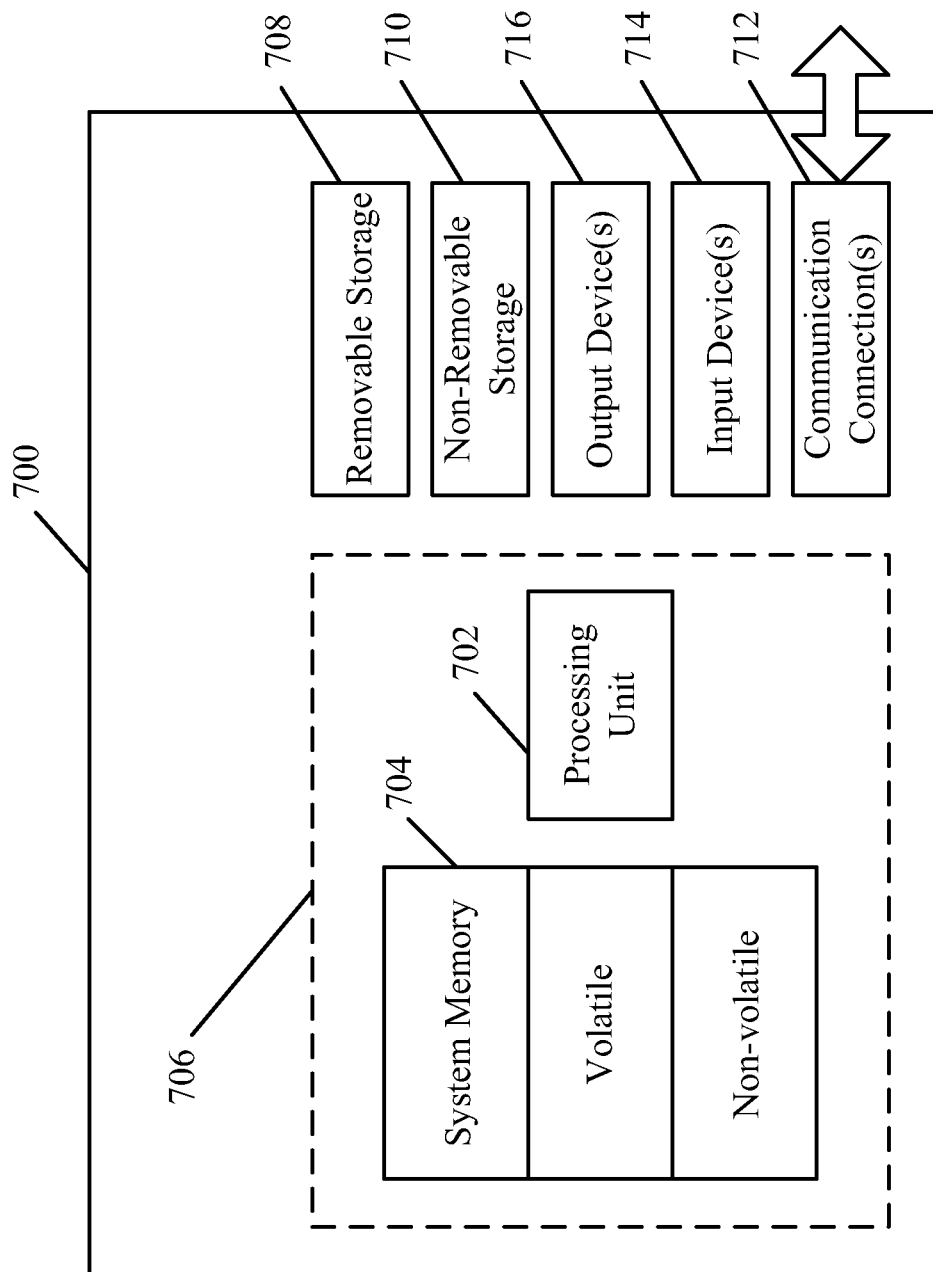
FIG. 7 is a block diagram of an example computing environment that may be used in connection with implementations of the subject matter described herein.

The subject matter described herein may be implemented through the use of a computer system, or other type of device that has some computing mechanism(s). FIG. 7 shows an example computing environment in which example embodiments and aspects may be implemented. The computing system environment is only one example of a suitable computing environment and is not intended to suggest any limitation as to the scope of use or functionality.

Numerous other general purpose or special purpose computing system environments or configurations may be used. Examples of well-known computing systems, environments, and/or configurations that may be suitable for use include, but are not limited to, personal computers (PCs), server computers, handheld or laptop devices, multiprocessor systems, microprocessor-based systems, network PCs, minicomputers, mainframe computers, embedded systems, distributed computing environments that include any of the previously-described systems or devices, and the like.

Computer-executable instructions, such as program modules, being executed by a computer may be used. Generally, program modules include routines, programs, objects, components, data structures, etc., that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 7, an example system for implementing aspects described herein includes a computing device, such as computing device 700. In its most basic configuration, computing device 700 typically includes at least one processing unit 702 and memory 704. Depending on the exact configuration and type of computing device, memory 704 may be volatile (such as random access memory (RAM)), non-volatile (such as read-only memory (ROM), flash memory, etc.), or some combination of the two. This most basic configuration is illustrated in FIG. 7 by dashed line 706.

Computing device 700 may have additional features/functionality. For example, computing device 700 may include additional storage (removable and/or non-removable) including, but not limited to, magnetic or optical disks or tape. Such additional storage is illustrated in FIG. 7 by removable storage 708 and non-removable storage 710.

Computing device 700 typically includes a variety of computer readable media. Computer readable media can be any available media that can be accessed by computing device 700 and includes both volatile and non-volatile media, removable and non-removable media. By way of example, and not limitation, computer readable media may comprise computer storage media and communication media.

Computer storage media includes volatile and non-volatile, removable and non-removable media implemented in any method or technology for storage of information such as computer readable instructions, data structures, program modules or other data. Memory 704, removable storage 708, and non-removable storage 710 are all examples of computer storage media. Computer storage media includes, but is not limited to, RAM, ROM, electrically erasable programmable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media may be part of computing device 700.

Computing device 700 may also contain communications connection(s) 712 that allow the device to communicate with other devices. Communications connection(s) 712 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. The term computer readable media as used herein includes both storage media and communication media.

Computing device 700 may also have input device(s) 714 such as keyboard, mouse, pen, voice input device, touch input device, etc. Output device(s) 716 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an API, reusable controls, or the like. Such programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

Although example embodiments may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and hand-held devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
   receiving an indication of a change in depth of a depth sensor installed in a foundation of a building;
   determining, based on the indication of the change in depth, a crack in the foundation; and
   determining, based on the crack in the foundation, damage to the foundation.

2. The method of claim 1, comprising installing the depth sensor in the foundation.

3. The method of claim 2, wherein the installing the depth sensor in the foundation of the building comprises installing the depth sensor in a foundation material prior to construction of the foundation.

4. The method of claim 2, wherein the installing the depth sensor in the foundation of the building comprises attaching the depth sensor to a surface of the foundation.

5. The method of claim 4, further comprising detecting motion in a direction perpendicular to the surface of the foundation.

6. The method of claim 1, wherein the damage to the foundation is due to water.

7. The method of claim 1, wherein a plurality of depth sensors comprising the depth sensor are installed in a grid pattern.

8. The method of claim 1, wherein a plurality of depth sensors comprising the depth sensor are installed in the foundation of the building, further comprising detecting motion outside of a plane in which the plurality of depth sensors are mounted.

9. A device comprising:
   one or more processors; and
   memory storing instructions, that when executed by the one or more processors, causes the device to:
   receive an indication of a change in depth of a depth sensor installed in a foundation of a building;
   determine, based on the indication of the change in depth, a crack in the foundation; and
   determine, based on the crack in the foundation, damage to the foundation.

10. The device of claim 9, wherein the instructions, that when executed by the one or more processors, further cause the device to detect motion in a direction perpendicular to the surface of the foundation.

11. The device of claim 9, wherein the damage to the foundation is due to water.

12. The device of claim 9, wherein the depth sensor is disposed between at least two layers of material forming the foundation.

13. The device of claim 9, wherein the foundation comprises concrete.

14. The device of claim 9, wherein the damage comprises lateral movement of the foundation with respect to a direction of a plane of a surface of the foundation.

15. A non-transitory computer readable medium storing instructions that, when executed, cause operations comprising:
   receiving an indication of a change in depth of a depth sensor installed in a foundation of a building;
   determining, based on the indication of the change in depth, a crack in the foundation; and
   determining, based on the crack in the foundation, damage to the foundation.

16. The non-transitory computer readable medium of claim 15, wherein the instructions, when executed, further cause operations comprising detecting motion in a direction perpendicular to the surface of the foundation.

17. The non-transitory computer readable medium of claim 15, wherein a plurality of depth sensors comprising the depth sensor are installed in a grid pattern.

18. The non-transitory computer readable medium of claim 15, wherein the instructions, when executed, further cause operations comprising detecting motion outside of a plane in which a plurality of depth sensors comprising the depth sensor are mounted.

19. The non-transitory computer readable medium of claim 15, wherein the damage is due to water.

20. The non-transitory computer readable medium of claim 15, wherein the depth sensor is disposed between at least two layers of material forming the foundation.

\* \* \* \* \*